(12) United States Patent
Wulfman et al.

(10) Patent No.: US 8,475,484 B2
(45) Date of Patent: Jul. 2, 2013

(54) LIQUID SEAL ASSEMBLY FOR A ROTATING TORQUE TUBE

(75) Inventors: Edward I. Wulfman, Woodinville, WA (US); Casey Torrance, Seattle, WA (US)

(73) Assignee: MEDRAD, Inc., Indianola, PA (US)

( * ) Notice: Subject to any disclaimer, the term of this patent is extended or adjusted under 35 U.S.C. 154(b) by 1331 days.

(21) Appl. No.: 10/798,623

(22) Filed: Mar. 10, 2004

(65) Prior Publication Data

US 2004/0230213 A1   Nov. 18, 2004

Related U.S. Application Data

(63) Continuation-in-part of application No. 09/826,487, filed on Apr. 4, 2001, now Pat. No. 6,818,001.

(60) Provisional application No. 60/453,846, filed on Mar. 10, 2003.

(51) Int. Cl.
*A61B 17/32* (2006.01)
*A61B 17/3207* (2006.01)

(52) U.S. Cl.
USPC .............................. 606/180; 606/159; 604/35

(58) Field of Classification Search
USPC .................... 606/159, 167, 170, 180; 604/19, 604/22, 264, 265
See application file for complete search history.

(56) References Cited

U.S. PATENT DOCUMENTS

| | | | |
|---|---|---|---|
| 4,445,509 A | 5/1984 | Auth | |
| 4,591,355 A | 5/1986 | Hilse | |
| 4,728,319 A * | 3/1988 | Masch | 604/22 |
| 4,857,045 A | 8/1989 | Rydell | |
| 4,976,720 A * | 12/1990 | Machold et al. | 606/194 |
| 5,062,648 A | 11/1991 | Gomringer | |
| 5,217,474 A * | 6/1993 | Zacca et al. | 606/159 |
| 5,295,958 A * | 3/1994 | Shturman | 604/103.07 |
| 5,490,859 A * | 2/1996 | Mische et al. | 606/159 |
| 5,667,490 A | 9/1997 | Keith et al. | |
| 5,938,670 A | 8/1999 | Keith et al. | |
| 6,001,112 A | 12/1999 | Taylor | |
| 6,066,152 A | 5/2000 | Strauss et al. | |
| 6,080,170 A * | 6/2000 | Nash et al. | 606/159 |
| 6,258,052 B1 * | 7/2001 | Milo | 604/22 |
| 6,565,588 B1 | 5/2003 | Clement et al. | |
| 6,818,001 B2 | 11/2004 | Wulfman et al. | |
| 2002/0007190 A1 | 1/2002 | Wulfman et al. | |
| 2002/0095147 A1 * | 7/2002 | Shadduck | 606/41 |
| 2004/0006358 A1 | 1/2004 | Wulfman et al. | |

\* cited by examiner

*Primary Examiner* — Kathleen Holwerda
*Assistant Examiner* — Sarah W Aleman
(74) *Attorney, Agent, or Firm* — Ann W. Speckman; Speckman Law Group PLLC

(57) ABSTRACT

A sealing assembly hinders or prevents air or other fluid from seeping between various components of a medical device by use of a liquid seal. An infusion port is for introducing a sealing liquid to immerse a flood space between a liner that surrounds a torque tube and/or within the torque tube, thereby creating a liquid seal around the torque tube and lubricating the torque tube. The length of the liner and the cross sectional space of the flood space are adjusted to control flow rate. An aspiration port may force suction pressure into a lumen extending along the length of the medical device in a distal direction. The liquid seal also prevents diluting of the suction pressure by stopping ingress of air.

15 Claims, 9 Drawing Sheets

LIQUID SEAL ASSEMBLY FOR A ROTATING TORQUE TUBE

This application claims priority from U.S. Provisional Patent Application No. 60/453,846, filed Mar. 10, 2003 and is a continuation-in-part of U.S. patent application Ser. No. 09/826,487, filed Apr. 4, 2001, now U.S. Pat. No. 6,818,001. The disclosures of these applications are incorporated herein by reference in their entireties.

FIELD OF THE INVENTION

The present invention relates to an assembly for sealing structural elements that move relative to each other. The present invention is particularly, but not exclusively, useful for establishing a liquid seal around a rotatable torque tube in a medical device. It is to be understood that the terms "medical field" and "medical device", as used herein, include traditional medicine as well as alternative medicines including chiropractic, acupuncture, etc., as well as the veterinary field.

BACKGROUND OF THE INVENTION

In numerous applications of devices in the medical field, it may be necessary or desirable to create a fluid-tight seal between structural components. For many medical devices, creating such as seal is manifestly critical to the safety and reliability of the devices. For example, it is often important for medical devices to incorporate a mechanism to prevent liquid or gasses, including air, from contacting certain device elements, entering the body through the device, seeping in, such as where suction pressure may be diluted, or leaking out of the device, such as where suction pressure may be lost.

In some particular applications, an intracorporeal device having rotational components is employed for therapeutic and/or diagnostic procedures. For example, devices to remove obstructions, including partial or total occlusions or other lesions of various types, from a target site in the body, e.g. a blood vessel, using a rotating cutter assembly is well established treatment modality in interventional cardiology. Numerous methods and devices have been conceived and developed.

Atherectomy or thrombectomy devices are often used for treatment of arterial occlusions. Atherosclerosis is a condition arising from the deposition of fat-like matter, i.e. plaque, on the walls of blood vessels. As a result of accumulated obstructions, blood flow becomes restricted or blocked, creating health risks, including coronary artery disease, angina and heart attacks. Most methods of using atherectomy and thrombectomy devices involve placement of a guiding catheter into the body and insertion of a guidewire, over which an operating head is guided to a target site where an occlusion is located within a blood vessel. However, devices that do not employ guidewires are also possible. A catheter surrounds a drive shaft to effectively isolate the rotating elements of the device from direct contact with any healthy body matter, e.g. tissue. The drive shaft is coupled to the operating head that is advanced, and in some devices, rotated to cut or ablate the obstruction and to restore or improve blood flow in the vessel.

It is important for atherectomy or thrombectomy procedures to include steps to collect dislodged particulates from accumulating in the body. Furthermore, findings have shown that stent deployment to treat Acute Coronary Sydrome ("ACS") is often associated with plaque embolization in patients with ACS. See Circulation 2003; 107:2320-5. This heart damage increases the risk of long-term adverse clinical outcomes. In another example, kidneys are known to be very susceptible to blockage if embolisms occur in a renal artery during renal interventions. In the case of treatment of deep vein thrombosis, complications also occur if a clot breaks off and travels in the bloodstream to the lungs.

Some current devices employ filter systems to catch loosened debris. However, filter systems may allow small particles to pass and may be poorly positioned against a vessel wall. Other current devices use aspiration as an effective means to suction away embolic particulates that have been extracted from the body and provide embolic protection. However, it is important for the aspiration to be consistently maintained and provided at high rate. Therefore, a tight seal must be provided so that aspiration is not lost through cracks in the joint between device components. Moreover, the seal must prevent air from getting into the aspiration area and competing with aspiration for space. Accordingly, specific interest of the present invention is in maintaining fluid-tight seals which are necessary for the proper operation of an atherectomy device.

Regardless of the particular application, problems which must be overcome to establish a fluid-tight seal are particularly difficult when the seal is required between components that move relative to each other. For example, particles of matter that have been excised along with blood are often forced to enter a catheter and, so, fluid-tight seals are necessary to prevent the loss of blood through the gaps where the catheter ends and a rotating drive shaft continues to engage a motor. A sealing assembly may be required to seal the drive shaft and the catheter that encloses the drive shaft. In practice, a connector of catheter components and associated joints in catheter systems are prone to leaks because the catheter area may be under pressure during its operation.

During operation of an aspirating catheter system, there are often zones of substantially different pressures within the catheter or between the catheter and the body. The pressure difference may result in leakage of air, blood, or other gas or liquid. For example, rotation of components of the device, such as a drive shaft, may produce high rotational forces within the catheter system. Catheters with rotational drive systems are particularly problematic to seal against different zones of pressure, as in the case of a drive shaft that provides a lumen for a guidewire to translate from a zone of atmospheric pressure to zones of body pressure or zones of very low pressure. At a junction formed where the guidewire exits out the proximal end of the drive shaft, air may seep into the lumen. The decreasing pressure differential from the proximal end to the distal end of the drive shaft encourages invading air to travel along the length of the device and into the body. To address such problems, a seal is typically positioned at the drive shaft's proximal terminal end.

One conventional method for sealing a conduit in proximity to a drive shaft involves the use of an O-ring to surround the drive shaft. However, where the drive shaft rotates at a high rate, contact between the O-ring and the drive shaft often causes frictional heating, which may be destructive to the seal. An O-ring sealing the outside of a drive shaft also has no accommodation for sealing the lumen between the drive shaft and a guidewire.

Furthermore, some other current sealing mechanisms use a bushing around the drive shaft to seal it. But these bushing systems require close and precise tolerance between the outer surface of the drive shaft and the opening of the surrounding bushing. Both the drive shaft and the bushing must be machined to have very accurate dimensions. Also, with the bushing-type seal, the drive shaft needs to be smoothly finished in order to bear closely against the bushing. See, for example, U.S. Pat. No. 4,591,355. The machining process for such as sealing element is complex.

Moreover, current sealing mechanisms do little to seal drive shafts that are not solid shafts. Coiled wire drive shafts have gaps between the coils that may permit leakage. Nor are such sealing mechanisms effective to seal an inner channel in a drive shaft that is used for a guidewire.

It is therefore desirable to provide simple, effective seal for a torque tube and that creates no friction as a torque tube rotates. The seal should be able to prevent air from seeping into a catheter and diluting efficient aspiration through the system. It would be desirable for the seal to be relatively easy to manufacture, durable, and comparatively cost-effective. The present invention fulfills these needs and provides further related advantages.

SUMMARY OF THE INVENTION

A sealing assembly is provided that uses a liquid as a sealing medium as well as a lubricant of moveable catheter components. In one particular embodiment, the sealing assembly forms an effective seal around a rotatable torque tube as it enters into an area of high vacuum, while effectively preventing loss of vacuum at the proximal end of the sealing assembly. The sealing assembly includes a liner wrapped around a rotatable torque tube. The liner extends longitudinally along at least a portion of the torque tube. A flood space is formed within the inside diameter of the liner, including any internal clearance areas, lumens or gaps in or around the torque tube. A housing, i.e. "sealing member", is also provided with an infusion port for infusing a sufficient amount of liquid in the flood space to create a seal around the torque tube. In one embodiment, a suction port is included in the sealing member for aspirating fluid from a lumen that extends within a catheter. The liner often separates areas of different pressures, such as lower pressure in the flood space from adjacent higher pressure outside or proximal to the flood space. At times, an intersect area is located at the distal terminal end of the liner and within the catheter. The pressure at the liner distal terminal end may be at least substantially equal to the pressure of the catheter lumen at the intersect area. Liquid in the flood space travels toward the intersect area and is forced to exit the flood space at the intersect area. The exiting liquid may travel into the lumen, where it may mix with suction force in the lumen. Oftentimes, the liner is sized to have a length that reduces flow rate of liquid traveling in a distal direction in the flood space and restricts the amount of liquid exiting the flood space.

BRIEF DESCRIPTION OF THE DRAWINGS

The present invention is illustrated by way of example in the figures of the accompanying drawings and the figures are not intended for limitation, which figures are not intended to limit the present invention, and in which:

FIGS. 2A to 2D are schematic diagrams of internal components of one sealing assembly according to one embodiment of the present invention and a medical device catheter system, wherein FIG. 2A shows the overall assembly, FIG. 2B shows an enlarged portion of an infusion site of the sealing assembly depicted in FIG. 2A, FIG. 2C shows an enlarged portion of an aspiration site of the sealing assembly depicted in FIG. 2A, FIG. 2D shows an enlarged portion of a distal junction of the sealing member depicted in FIG. 2A.

FIGS. 4A to 4C are schematic diagrams of a sealing member according to one embodiment of the present invention, wherein FIG. 4A shows a sealing member with port attachments, FIG. 4B shows an internal view of components exploded from the member of FIG. 4A, and FIG. 4C shows an external view of exploded components of the member of FIG. 4A;

FIGS. 5A to 5B are schematic diagrams illustrating a tracking pod, according to some embodiments of the present invention, wherein FIG. 5A is an internal view of the tracking pod casing, and FIG. 5B is an internal view of the tracking pod illustrating the components of the tracking pod mounted therein.

DETAILED DESCRIPTION OF THE INVENTION

A sealing assembly is provided to hinder air or other fluid from seeping between various components of a medical device. In one aspect of the sealing assembly, a liquid seal site prevents air from traveling along a torque tube, such as down a drive shaft of a catheter system. A liner surrounds the torque tube and an infusion port permits a sealing liquid to immerse a flood space within the inside diameter of the liner, i.e. between the liner and the torque tube and/or within the torque tube, thereby creating a liquid seal around the torque tube. In one embodiment of the sealing assembly, an aspiration port is provided to force suction into a lumen extending along the length of the medical device in a distal direction. The liquid seal prevents diluting of the suction pressure by stopping ingress of air.

With this sealing assembly, a high tolerance seal is not required for the torque tube and there is no significant friction added. Thus, the clearances of the seal of the present invention may be at least an order of magnitude larger than other previous torque tube seals that are precisely machined. Such low and non-stringent tolerance requirements also permit a coiled drive shaft to be sealed rather than being limited to a solid shaft as well as sealing of a guidewire lumen.

Figure 1:
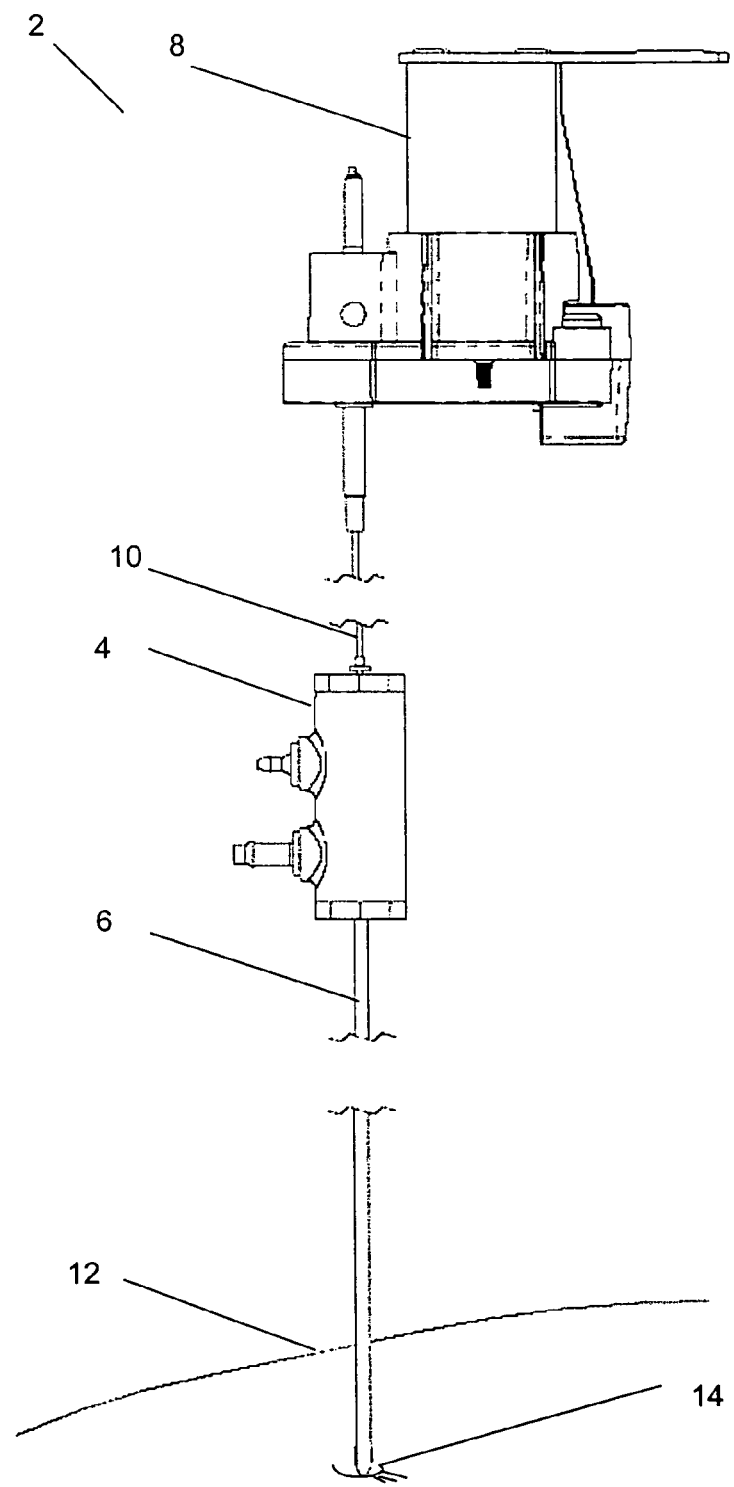
FIG. 1 is a schematic diagram of an external view of a sealing assembly implemented in an intracorporeal medical device, according to one embodiment of the present invention.

As shown by example in FIG. 1, one particular medical device 2 that may incorporate a sealing assembly 4 of the present invention is an intracorporeal medical device having a catheter system 6 extending from at least the sealing assembly to inside of a patient's body. The medical device includes components that are inserted and navigated within the patient's body while an operator uses the medical device, and these components are generally continuous with and/or in communication with components for placement external to the patient.

As used herein to describe various components of the medical device including the sealing assembly affixed to the medical device, the term "proximal" refers to a direction or area away from the end of the device to be first inserted into a body, and "distal" refers to the direction or area toward such insertion portion.

The extracorporeal components of the medical device 2 essentially comprise a drive system 8 that rotates a torque tube 10 at the proximal end of the torque tube. The proximal end of torque tube 10 passes through the sealing assembly is operably connected or coupled to drive system 8. A catheter 6 surrounds the torque tube from the sealing assembly and extends distally into the body 12. The catheter enclosing the torque tube is inserted into the body at an insertion point 14.

The drive system 8 may be a motor e.g. a high-speed electric motor or a pneumatic-powered motor. However, the drive system may also be any means of manually, such as by hand, or automatically rotating the torque tube.

The torque tube 10 may be any elongated tube that is rotatable. Oftentimes, the torque tube is a drive shaft comprising multiple coils or filars. Drive shaft is typically a flexible, hollow, helical, torque-transmitting shaft. Hollow, multi-filar metallic drive shafts are known in the art and are suitable for use with the present sealing assembly since the sealing assembly permits sealing of non-solid shafts as well as solid shafts. A multi-filar stainless steel coil drive shaft having a bi- tri- or quad-filar construction is often employed. A coil drive shaft having an inner diameter of from about 0.015 to 0.025 inch and an outer diameter of from about 0.025 to 0.035 inch is typical for atherectomy applications. In some applications, the drive shaft may be rotated at high speeds of about 500 rpm to 200,000 rpm may be used, more typically about 10,000 to 100,000 rpm and more often about 40,000 rpm, or more.

The sealing assembly 4 may be positioned at various locations along the length of the catheter system that is external to the body. Typically, the sealing assembly is positioned close to the drive system, where the pressure may be generally higher than the more distal end of the device and air is likely to seep into the device.

The sealing assembly may be positioned at various locations along the length of the catheter system that is external to the body. Typically, the sealing assembly is positioned close to the drive system, where the pressure may be generally higher than the more distal end of the device and air is likely to seep into the device.

Figure 2A:
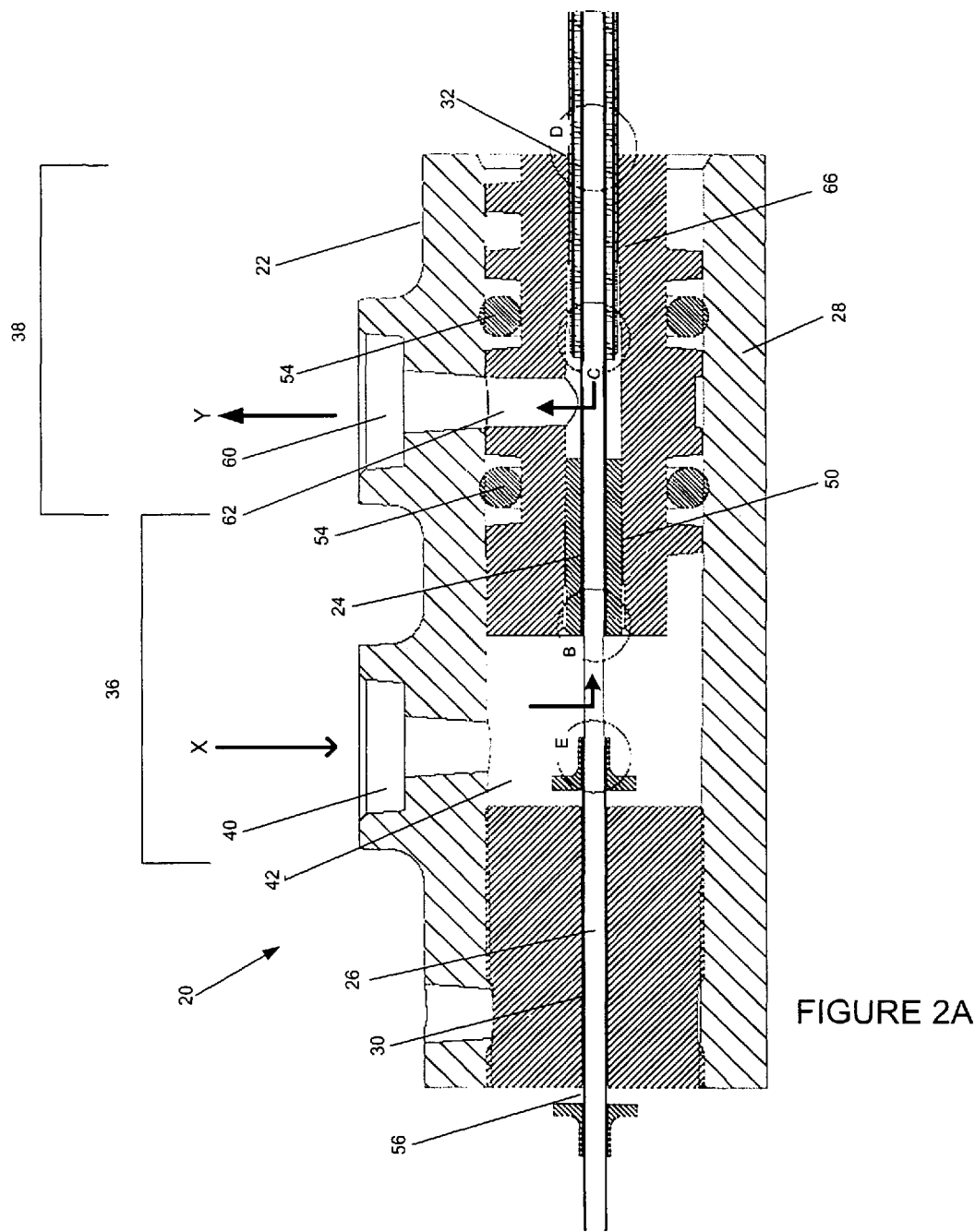

FIG. 2A shows one embodiment of sealing assembly 20 having a sealing member 22 and a liner 24 wrapped around a torque tube 26. The sealing member includes a housing 28 to encase one or more sealing sites where each sealing site is for sealing components of the catheter system. The housing is a rigid member that encloses at least a portion of the torque tube in a manner that permits free rotation and typically axial translation (i.e., in a lateral direction) of the torque tube. The housing includes a longitudinal bore 30 through which the torque tube is positioned. The bore includes one or more axially aligned sites, to form the one or more sealing/junction sites. At least one layer of the catheter system containing the torque tube passes into the sealing assembly at a front end aperture 32. The proximal end of the catheter system terminates in the sealing assembly at an aspiration site 38. The torque tube continues through the sealing assembly and passes through a back end aperture, such as overflow port 56.

Liquid is applied through the sealing assembly at the area where the device is under substantially atmospheric pressure and susceptible to leaks. The liquid seal site prevents air from traveling along a significant length of the torque tube area towards the body. An infusion port 40 leads to a reservoir 42 for introduction of the liquid.

Figure 2B:
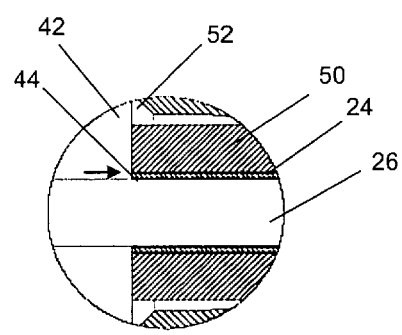

A partial enlarged view of a liquid seal site 36 is shown in FIG. 2B. In general, a tubular liner 24 is spaced apart from and surrounds at least a portion of the longitudinal length of the torque tube. A flood space 44 is provided between the liner and torque tube, and/or optionally within any coils or gaps of the torque tube and a guidewire lumen. In a direction shown by arrow X, liquid is injected into infusion port 40, and from the reservoir 42 liquid is permitted to crawl into the flood space 44.

Prior to the operation of the medical device, the device is prepared for use by introducing liquid into the infusion port and allowing the liquid to move into the crawl space. As the medical device is used, the liquid continues to flow into the sealing assembly from the infusion port. Liquid from the infusion port may be drawn into sealing assembly by various mechanisms, such as capillary action, action of a pump, gravity and/or other forces. Typically, the liquid flows from a liquid source and through tubing connected to the infusion port. In one embodiment, liquid drips from a conventional container that is placed a certain distance above the height of the sealing assembly, whereby the rate of liquid flow into the sealing assembly is controlled by the height position of the container.

In one embodiment of sealing assembly, any convenient type of liquid may be infused through the infusion port. For example, saline or water is common. In another embodiment, the liquid may comprise blood and/or plasma that is extracted from the patient. For example, blood and/or plasma that is aspirated from the patient through the medical device may be treated, such as filtered, mixed with chemicals, e.g. anticlotting agents, and/or defoamed. This treated blood and/or plasma may be channeled back to the sealing assembly, e.g. via tubing, and introduced into the infusion port as liquid for the seal.

Typically, the liner is not bonded to the torque tube so that the torque tube is permitted to freely rotate and the liner remains stationary. With the use of a liner, the infused fluid may creep down the torque tube and, where the torque tube is a multi-filar drive shaft, the fluid moves within the coils of the drive shaft and optionally into a guidewire lumen, if provided. In this manner, air may be prevented from getting into the conduit external to the torque tube and within the catheter. However, surface tension and head loss may hinder the liquid from moving very rapidly down the flood space, and minimize the amount of liquid flowing through the flood space even when high vacuum is provided on the distal end of the tube.

The liner may comprise any material that is formable into a thin, tough, flexible tube. The liner is typically highly flexible so that the liner follows the contour of the torque tube without adding resistance to the flexing of the torque tube. The liner may be supported along its length by the internal drive shaft, and so, the liner need not be stiff. The liner may also include a material that is lubricious. The liner material should also be durable and resist significant wear. Where the torque tube rotates at a high speed, the liner material possesses high thermal resistance to not melt from any frictional loads created by torque tube rotation. The liner may include conventional polymer-based tubing. In one embodiment, the liner comprises a polyimide tube and includes a coating of a polytetrafluoroethylene (PTFE) or Teflon® layer (by e.i. DuPont De Nemours and Company Corporation located in Wilmington, Del.) along at least the inner diameter of the liner (such as polyimide tubing available from Microlumen Corporation, located in Tampa, Fla.).

The dimensions of the liner depend, inter alia, on the diameter and design of the catheter system including the torque tube, the required seal and any required aspiration. The clearance provided between the liner and the drive shaft for the flood space may be any convenient amount to provide a barrier from air seeping in, such as about 0.002 to 0.003 inch. The liner has an inner diameter and outer diameter that is sufficient to fit within the catheter. For example, for a torque tube of approximately 0.030", the inner diameter of the liner may be 0.034 inch and outer diameter may be 0.037 inch. Typically, the wall thickness of the liner is very small, such as 0.001 to 0.0015 inch.

The liner extends an operable distance along the axial length of torque tube. The liner may be any length that is sufficient to prevent air from moving the full distal length of liner and escaping out the distal terminal end of the liner and long enough to slow the infusion of sealing liquid as not to be excessive. For example, the liner may be about 1 to 30 inches in length, more typically 6 to 25 inches in length, and more often about 25 inches. However, in embodiments that include aspiration within a lumen in the catheter system, the liner may consume some of the available lumen space for aspiration. In this case, considerations of the aspiration requirements verses sealing requirements (as by head loss principles, described below) may be considered in determining liner length, where a longer liner may compromise aspiration rate by consuming room within the catheter system needed for aspiration. Accordingly, if room for aspiration needs to be increased, a shorter liner may be desired.

The sealing assembly utilizes the liner and pressure differentials within the device to create the liquid seal. Generally, a zone of substantially atmospheric pressure is located at the junction where the proximal end of the torque tube exits the sealing member due to ingress of air from the environment. The pressure within the flood space decreases along the length of the liner in a distal direction. As expected by theories of head loss across a length, the rate of flow in the flood space defined between two ends of the liner can be related to the pressure difference between these two points. The following known pipe head loss principle represents resistance to fluid flow:

$$h_c = f(LV/d2g),$$

wherein head loss value ($h_c$), (f) represents a friction constant, (L) represents length between two points, (V) represents velocity of liquid, (d) represents diameter between the two points and (g) represents gravity. According to this principle, a large length (L) and a small diameter (d) results in a higher head loss ($h_c$).

It is generally preferred that the liquid flow rate within the flood space be slow to create a more effective seal and to minimize the amount of liquid exiting the flood space and diluting the aspiration. One embodiment of the present invention seeks to increase the flood space length (L) and/or reduce the cross-sectional diameter (d) of flood space. A small diameter may be formed by fitting the liner close to the torque tube and fitting the torque tube close to a guidewire, where such as guidewire is present. For example the inner diameter of the liner may be between about 0.030 and 0.040 inch. Moreover, length of the liner may as long as necessary to decrease flow rate along the length of the flood space. A longer liner may be, for example, between about 6 to 30 inches and more often about 15 to 25 inches. Thus, the amount of liquid traveling out the distal end of the liner is restricted.

Although rotation of the torque tube may increase pressure in this flood space area, in some embodiments, the torque tube may be alternately rotated in opposing directions, i.e. clockwise and counter clockwise, and the pressure due to rotation may not be of much assistance.

Pressure differences through the medical device are an important aspect of the present invention. The liner seals the flood space to separate the pressure within the flood space from the surrounding pressures. For example, the liner separates lower pressure in the flood space from adjacent higher pressure, such as suction pressure in a catheter lumen, outside or proximal to the flood space. In embodiments in which an aspiration force is included in a lumen in the catheter system, the pressure in the lumen gradually decreases in a proximal direction towards the aspiration source. Using absolute zero as a reference point, the aspiration source, according to one embodiment of the present invention, may create a vacuum near absolute zero. The pressure at the distal end of the medical device that terminates in the body may be substantially body pressure (e.g., about 2.3 psi above atmospheric pressure for systolic body pressure, where atmospheric pressure is about 14 psi relative to absolute zero). Furthermore, the infusion source may be placed at a height to overcome body pressure so that fluid may ingress into the body, especially when used as an intravenous device.

Figure 3:
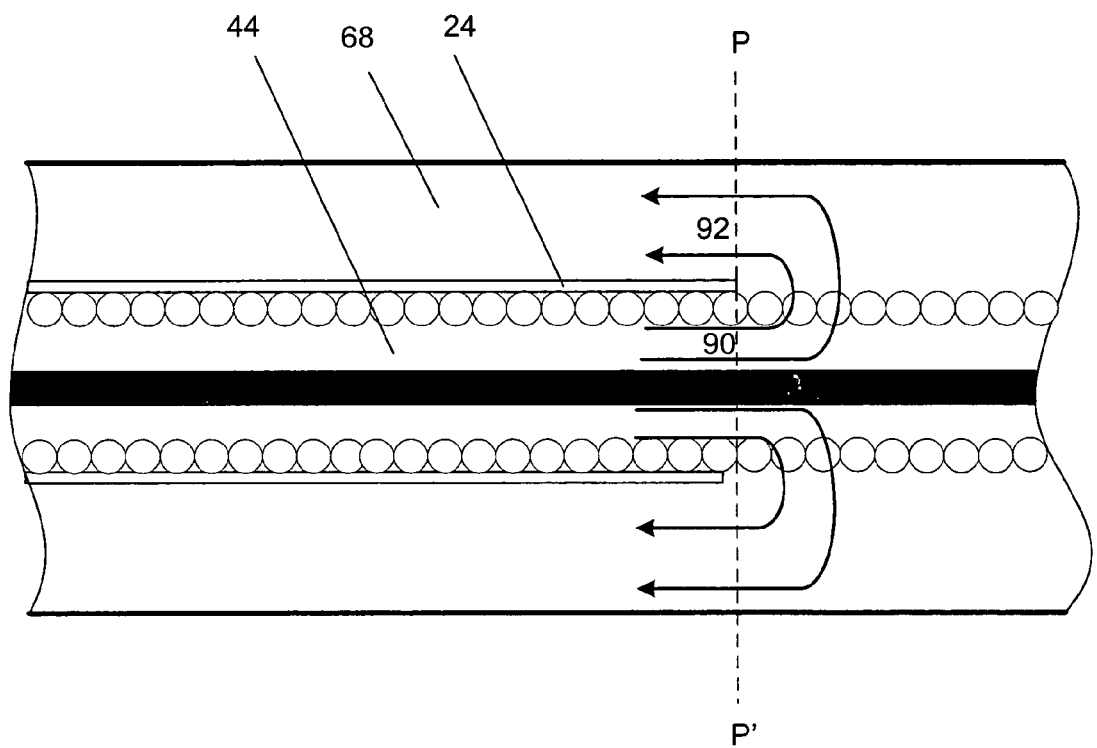
FIG. 3 is a schematic diagram of the distal terminal end of a liner within a catheter according to one embodiment of the present invention.

As shown in FIG. 3, at intersect area, P to P', a cross-sectional area of the medical device where the distal end of the liner 24 terminates, pressure 90 is usually at least substantially the same as the pressure 92 within the catheter lumen. Since the pressure internal to the liner and external to the liner are at least substantially equal, liquid exits the flood space 44 at this terminal end of the liner and becomes aspirated back through the lumen 68. In a sense, the liquid may travel a "U" turn by leaving the flood space and combining with the aspirated fluid.

As shown in FIGS. 2A and 2B, the sealing assembly may further include an insert 50, such as a tube, over a section of the liner. The insert may comprise any rigid material, such as metal. The insert may be held in tight association with at least a portion of the liner, such as by any conventional mechanical and/or chemical bonding, sealing, adhering, clamping, retaining technologies. For example, the internal surface of the insert may be bonded to liner with the use of an adhesive. Furthermore, one or more O-ring(s) 54 may be provided at the inner housing portion that surrounds distal end of the tube to further compress the housing against the insert. In addition, an adhesive substance or U.V. bond may be applied to any gaps 52 in the reservoir walls that may be formed during the manufacture of the housing, to seal the gaps. Any biocompatible adhesive may be used for these purposes, such as cyanoacrylate glue.

In one embodiment, one or more overflow port 56 may also be generally provided to allow excess liquid in the reservoir to leak out of the sealing assembly. In one embodiment, the overflow port is the back end aperture where the torque tube exits the sealing assembly. The overflow port may be any convenient diameter and shape, such as 0.030-0.040 inch or where the torque tube extends through the overflow port, the overflow port may provide clearance of 001 to 0.002 inch around the torque tube.

In some embodiments of sealing assembly, vacuum may be applied during operation to one or more aspiration ports 60, creating a zone of low pressure within the catheter system and inducing fluid flow along a lumen in a proximal direction shown by arrow Y. The suction encourages matter to move from the body, into the medical device and down the lumen of the catheter, and into the aspiration port. The material flows into channel 62 and into aspiration port 60. The aspiration force may be created by an aspiration source, such as a roller pump, vacuum pump, or the like. The aspiration source is coupled to the aspiration port, such as via tubing.

One or more optional compression elements urge components into close contact to prevent the suction force from leaking out. O-rings 54 may be provided at various points around the channel 62 to serve as compression elements.

Figure 2C:
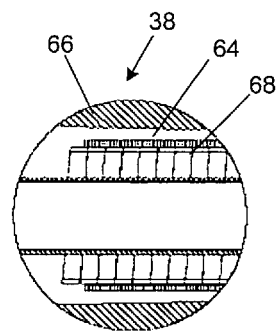

As shown by the enlarged view of a portion of an aspiration site 38 in FIG. 2C, the aspiration site creates a fixed joint for the proximal terminal end of a catheter layer 64 wrapped around the torque tube. Although a small gap may be formed between the inner housing walls 66 and catheter layer 64 during manufacture, at the terminal end of the catheter, at another point in the sealing member, the inner housing walls engage the catheter to form a fluid-tight seal between the internal catheter lumen 68 and the exterior of the catheter.

Figure 2D:
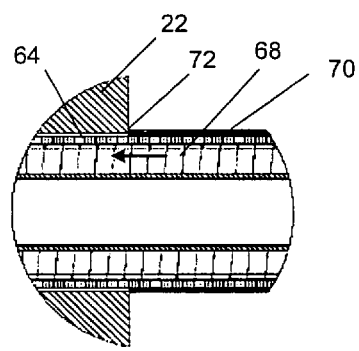

At times, the catheter may include multiple outer layers along various portions along the length of the catheter. As shown by the enlarged view in FIG. 2D, the proximal terminal end of at least a first outer layer 70 may abut the sealing member 22 at a junction 72. However, at least one layer 64 that defines the lumen 68 continues in a proximal direction from the junction to terminate at the aspiration site, as shown in FIG. 2C described above. In this manner, the lumen extends to the aspiration site for fluid flow in the proximal direction, indicated by the arrow as shown. Furthermore, an adhesive, U.V. bond or other bonding means may be applied at the junction 72 to seal the area and prevent aspiration from escape.

Figure 2E:
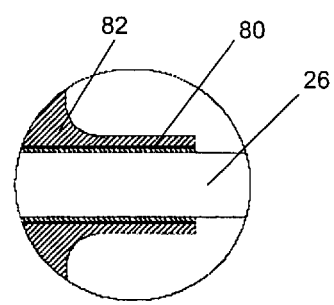
FIG. 2E shows an enlarge portion of the infusion site depicted in FIG. 2A having a main shaft.

As shown by the enlarged view in FIG. 2E, in some embodiments, an optional main shaft 80 may be secured to the torque tube, e.g. via welding, such that the main shaft rotates with the rotation of the torque tube. The main shaft may also be affixed to one or more retainers 82. In this manner, the torque tube 26 may be secured to and prevented from disengaging from a drive system.

Figure 4A:
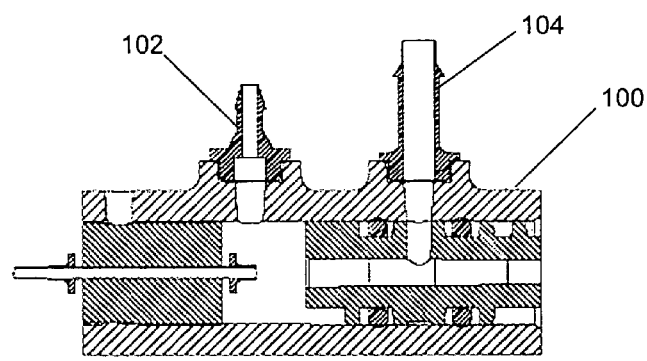

One embodiment of sealing member 100 is shown in FIG. 4A. An infusion attachment 102 may conveniently fit within the infusion port to form a sealed joint between the infusion port and tubing. Furthermore, an aspiration attachment 104 may also be placed within the aspiration port to form a sealed joint between the aspiration port and tubing. In one embodiment, the sealing member comprises a single molded part. However, for ease of manufacture, some embodiment of the housing of the sealing member may comprise several sections that are mounted together.

Figure 4B:
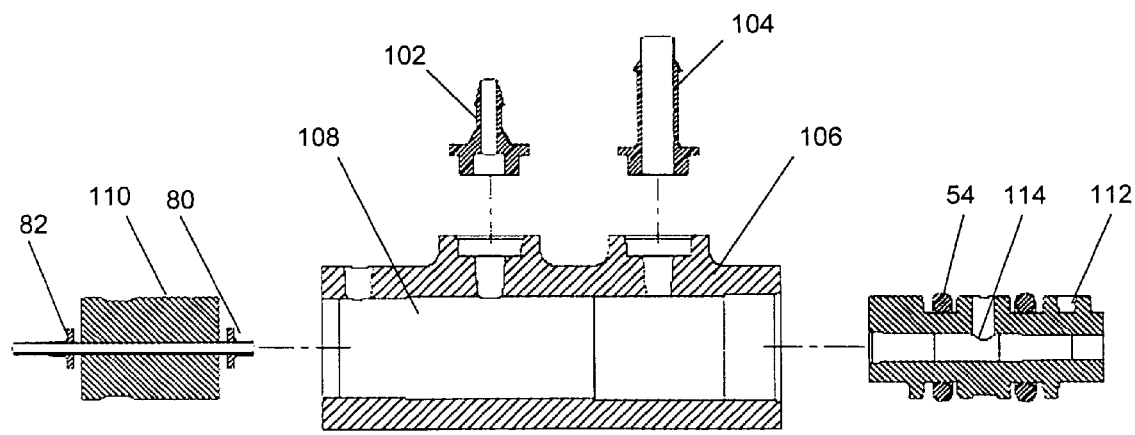

FIG. 4B shows an example of components exploded from one embodiment of a multi-part sealing member. For example, a main body 106 may include one or more hollow space(s) 108 into which one or more a plug element(s) 110, 112 may be placed. Proximal plug element 110 may optionally include the main shaft 80 mounted to the torque tube. One or more optional shaft retainers 82 may prevent the torque tube from sliding relative to the drive system. Furthermore, distal plug element 112 may include a channel 114 for aspiration and one or more compression elements 54, e.g. O-ring. In one embodiment, the proximal plug may be inserted in the main body space at a position that is proximal to the infusion port and the distal plug element inserted at a position that is distal to the infusion port, such that the infusion reservoir is formed between the distal end of the proximal plug element and the proximal end of the distal plug element.

Figure 4C:
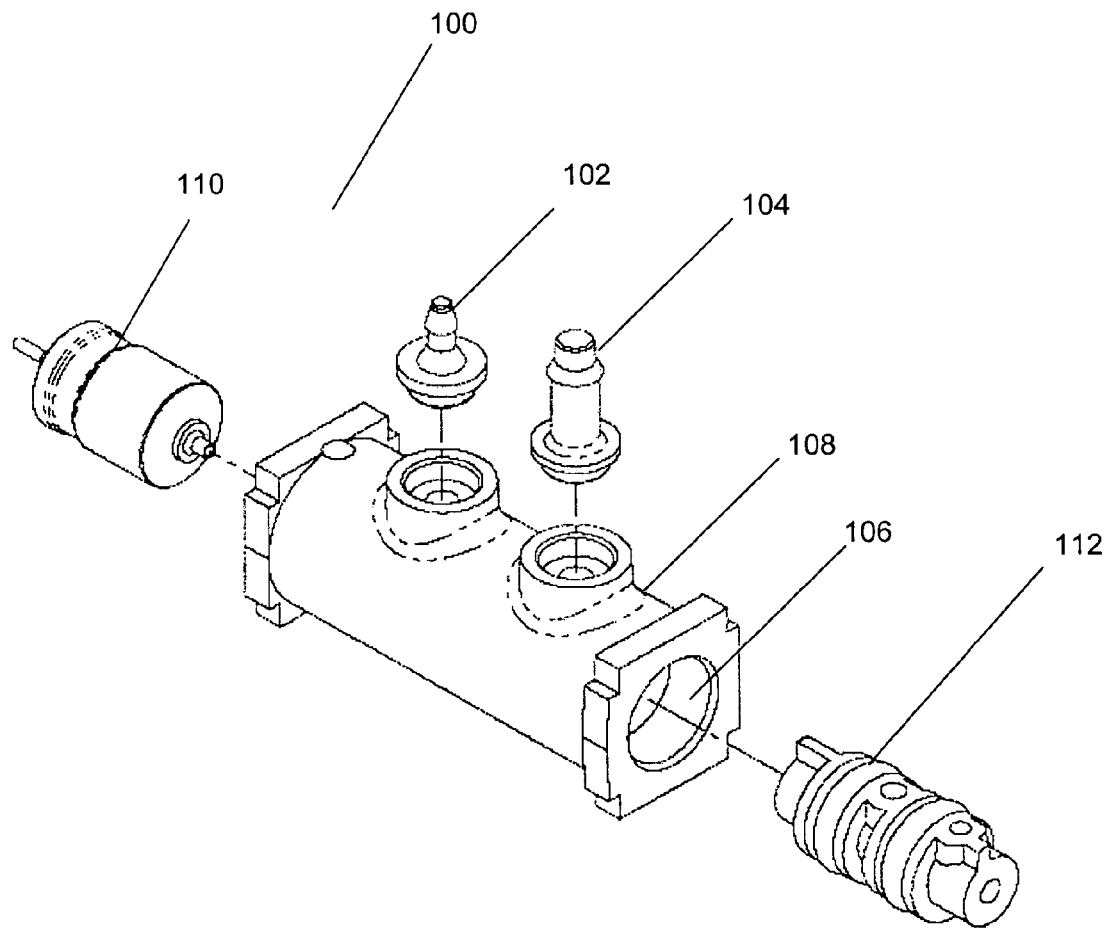

FIG. 4C shows an external view of a multi-part sealing member 120 with exploded components. A main body 106 houses a proximal plug element 110 and distal plug element 112 within hollow space 108. In addition, an infusion attachment 102 and an aspiration attachment 104 may be inserted within the main body 106.

Figure 5A:
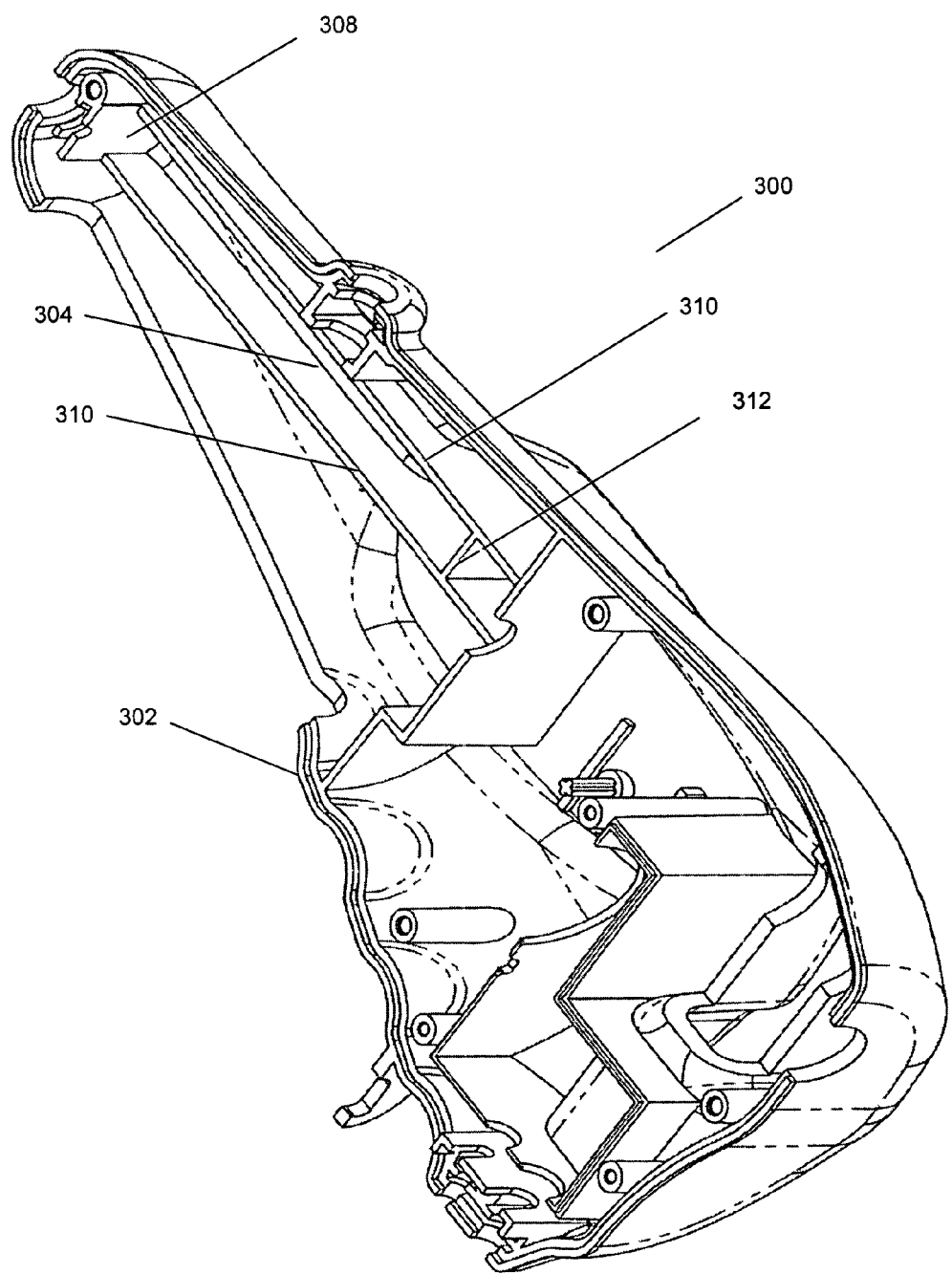
Figure 5B:
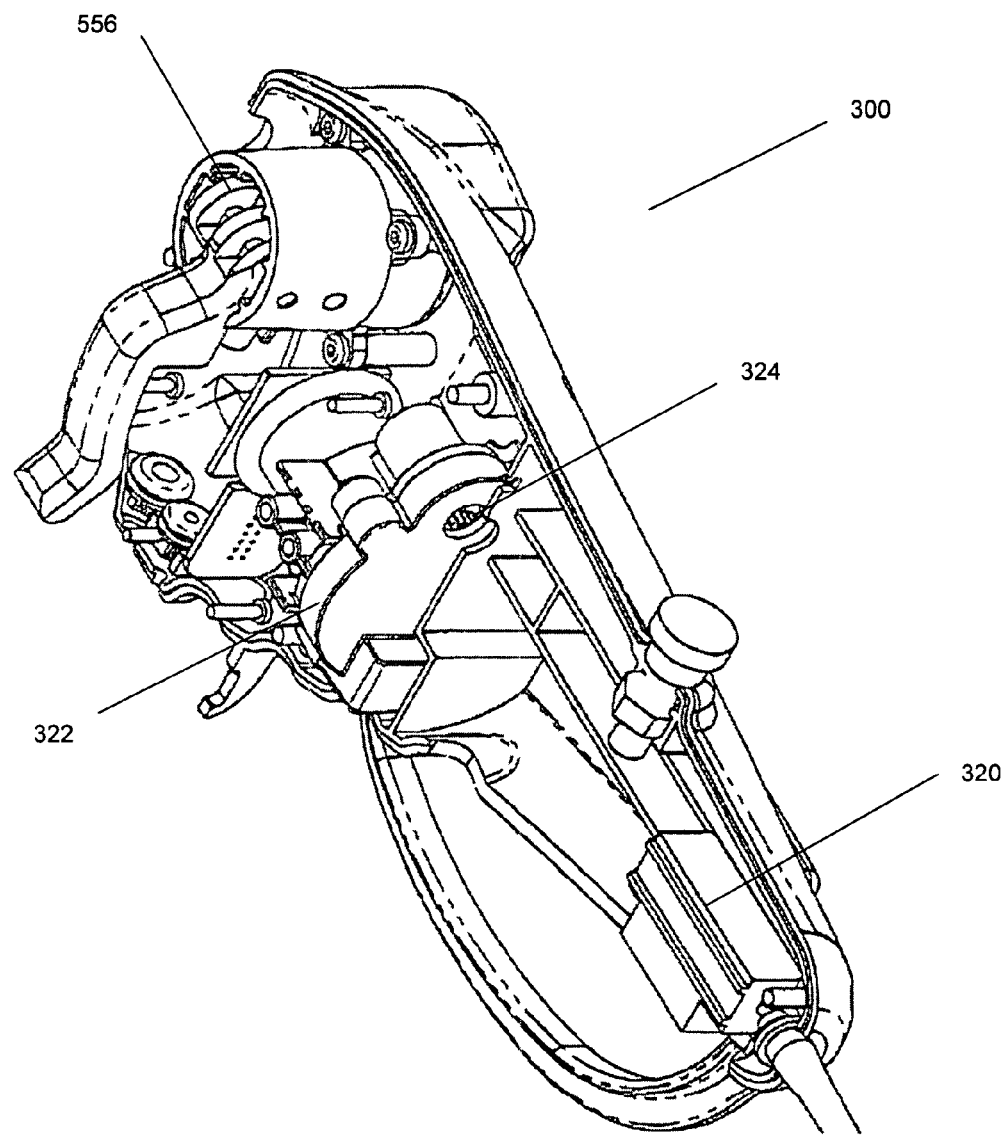

In one embodiment, the sealing assembly may be positioned inside of a hand held unit, such as a tracking pod 300 as shown by example in FIGS. 5A and 5B. The components of the tracking pod 300 are provided in a casing 302, including a top shelf, i.e. top half of the casing, or bottom shelf, depicted in FIG. 5A. The tracking pod may comprise a structure having one or more axial translation mechanisms to axially translate the torque tube with the drive system, such as a bed 304 on which rides the sealing member of the sealing assembly. The bed may have a proximal edge 312 and distal edge 308 that define the length in which the sealing member may slide inside of the tracking pod as the catheter is axially translated. The bed may be provided on either or both the top shelf and bottom shelf of the casing.

The sealing member may include one or more grooves (not shown) that reciprocally engage one or more rails 310 in the bed 304 in the tracking pod 300. In one embodiment, the bed may include a pair of rails on the top shelf and/or a pair of rails on the bottom shelf of the casing 302 of the tracking pod. The bed may further include a stop at one or usually both the proximal and distal ends of the bed to catch the sealing member traveling on the rails to one or both of the ends of the bed. The bed may be any convenient length that is longer than the length of the sealing member. The length of the bed dictates the length of catheter that may be directed into the body during operation of the medical device, without unlocking the tracking pod and repositioning the sealing member to the proximal end of the bed.

As shown in FIG. 5B, the tracking pod may further include the drive system 322. The torque tube extends from the sealing assembly 320 into the opening 324 of the drive system. The tracking pod may also include one or more drainage apertures and/or reservoirs to facilitate drainage of infusate, e.g. saline, from the sealing assembly.

The tracking pod may be a convenient ergonomic design and constructed for placement in proximity to and/or in contact with the external body. In one embodiment, the tracking pod includes a handle for convenience in holding the tracking pod. The tracking pod according to the present invention is usually compact in size. The shape and size of the tracking pod often permits an operator to easily manipulate the torque tube while holding the tracking pod. In one embodiment, the tracking pod is about 20 cm in length.

The medical device incorporating the sealing assembly of the present invention may be implemented for treatment or diagnosis in a variety of medical operations and procedures, such as translumenal microsurgery. For example, the device may be used in the treatment of blood vessel conditions, such as removal of accumulations of materials in coronary blood vessels and in blood vessels remote from the heart, such as cranial vessels, and peripheral vessels. Other applications include, and are not limited to, the treatment or diagnosis of benign prostate hyperplasia; gynecological conditions involving accumulation of material in fallopian tubes and elsewhere, such as fibrotic disease; urological conditions, such as kidney stones; the treatment of gallbladder conditions, such as gall stones; and spinal cord and dural tube conditions, such as stenoses of the spinal canal.

Some medical devices are used to remove undesired matter from the body. The undesired matter may be any intracorporeal matter that may be removed by the present invention is any material contained within a body cavity that is desired to be removed and is often foreign matter, e.g. artherosclerotic disease, calcified plaque, thrombus, a gallstone, and other debris, a valve or portion thereof, etc. Some medical fields of use include cardiology, radiology, urology, neurology, etc.

Figure 6:
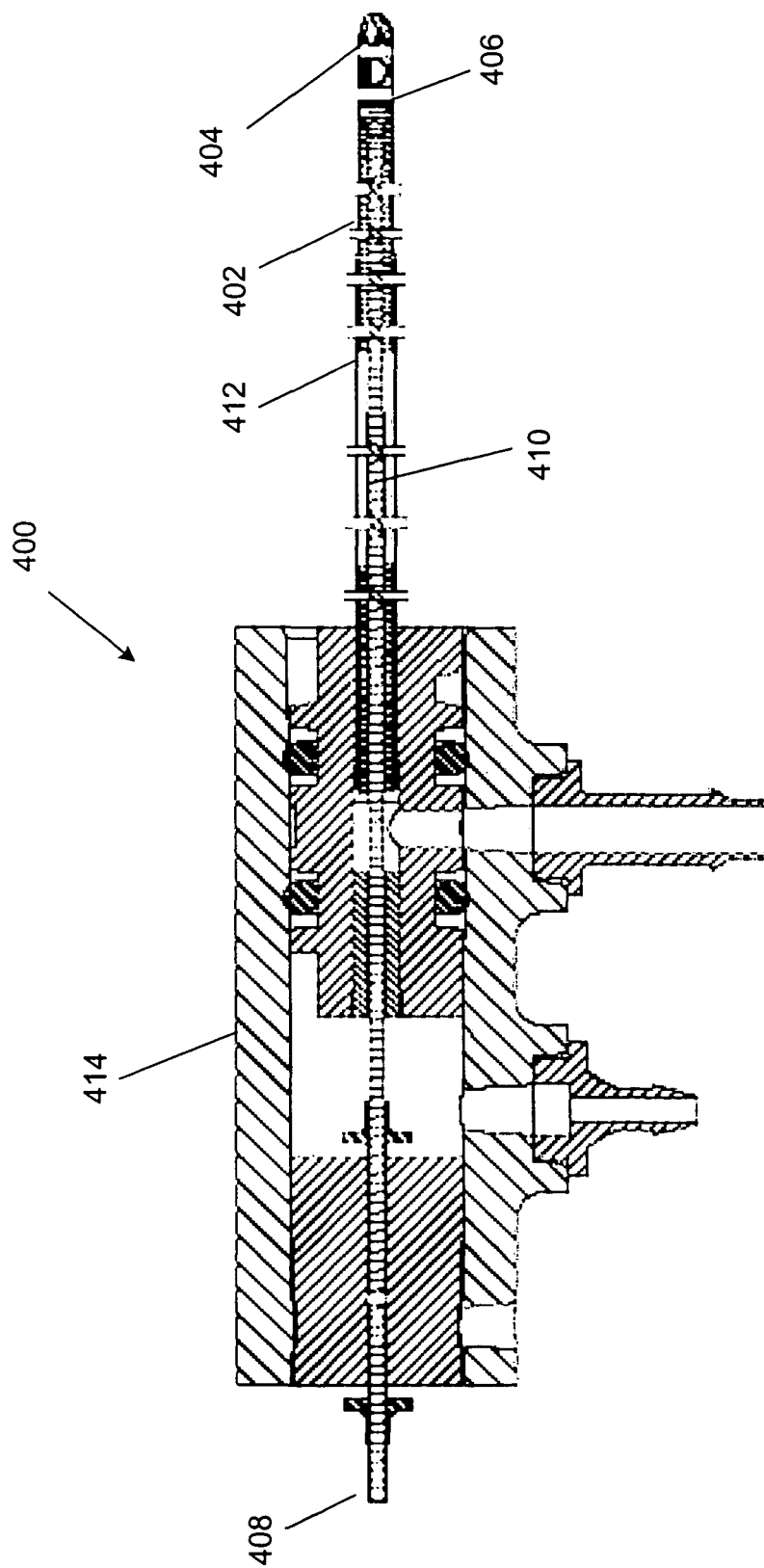
FIG. 6 is a schematic diagram illustrating one medical removal device that may incorporate the present sealing assembly.

One medical device 400, as shown by one exemplary device in FIG. 6, typically includes a catheter system 402 extending from an operation head 404 at a distal end 406 and a power source e.g. drive system, at a proximal end 408. A sealing member 414 is located along the length of the catheter. The catheter system often includes multiple layers of components such as the drive shaft 410, one or more sheaths, optional guidewire, etc. The catheter system has at least one lumen 412 in which fluids may flow to and from the operating head. The drive shaft is also provided, extending from the drive system to the operating head. A more detailed description of one type of medical device in which the sealing assembly of the present invention may be used is provided in U.S. Pat. No. 6,565,588 B1, filed on Nov. 28, 2000.

The torque tube usually conveys high speed rotation, e.g. about 500 to 200,000 rpm's, such as about 40,000 rpm's, to the operating head, especially where the operating head is designed with cutting surfaces to ablate the matter. Although, slower rotating torque tubes are also intended within the scope of the present invention.

A wide variety of operating heads for diagnostic or therapeutic surgical procedures within a body cavity that receives rotational torque from a torque tube is well known to those skilled in the art. For example, types of operating head may include a cutting head having one or more cutting surfaces, such as a rotary cutter with one or more blades or abrasives; a heating element for performing thermal ablation; electrodes for performing electrosurgical cutting and cauterization; abrasive elements for performing mechanical ablation; fluid jet stream tip; optical waveguides for performing laser ablation; ultrasonic transducers for imaging and ablation; angioscopic imaging devices; and the like.

One example of a medical device useful in diagnosis may include a probing operating head, such as an ultrasonic transducer. The diagnostic device may be useful in several medical fields. For example, in cardiology the operating head may be used to inspect the inside of the heart to identify abnormal structures or functions. The device may also be useful in measuring blood flow through the heart and other vessels. In urology, the device may be used to see kidney stones, measure blood flow through the kidney, detecting prostate cancer, etc.

Where the sealing assembly is implemented in an intracorporeal medical device, the device may be for use within any body cavity that has a sufficiently hollow space to accept the operating head and is suspected of containing undesirable solid matter. Some body cavities include a vascular cavity, gastrointestinal cavity, air exchange cavity, or the like. The body cavity may be a tubular-shaped structure, such as an artery, a vein, or another blood vessel, or another lumen structure, such as a ureter, a fallopian tube, a nasal passageway, and other tubular tissues in a body. For example, the system may be used for removing unwanted material in saphenous vein graft operations, from native coronary (and other) arteries, etc. The body cavity may also be an organ, such as a kidney, gall bladder, lung, or the like, or the body cavity may form part of another system, such as a lymph node, spinal canal, etc. The term "body", as used herein, includes that of a human being or another animal subject.

The present invention has been described above in varied detail by reference to particular embodiments and figures. However, these specifics should not be construed as limitations on the scope of the invention, but merely as illustrations of some of the present embodiments. It is to be further understood that other modifications or substitutions may be made to the described the sealing assembly and medical device, as well as methods of their use without departing from the broad scope of the invention.

We claim:

1. A medical device comprising:
   (a) a torque tube operably connected at a proximal end to a drive system for rotation and at a distal end to a working head;
   (b) a sealing assembly comprising:
      (i) a housing enclosing at least a proximal portion of the torque tube and a sealing site;
      (ii) a stationary liner surrounding and spaced apart from the torque tube extending longitudinally from the sealing site along a portion of the torque tube and terminating at an intersect area located proximal to the distal end of the torque tube;
      (iii) a liquid flood space located between the liner and the torque tube;
      (iv) an infusion port providing application of liquid to the liquid flood space at the sealing site during operation of the device; and
   (c) a catheter terminating at a proximal end at a fixed joint at an aspiration site within the housing and being in a fixed relationship to the stationary liner, the catheter extending distally beyond the intersect area to enclose the liner and form an aspiration lumen extending between the aspiration site and the working head whereby, during operation of the medical device, liquid enters the liquid flood space formed by the liner at the sealing site and creates a liquid seal around the torque tube to prevent ingress of air, and the liquid exits the liquid flood space at the intersect area, where it directly enters the aspiration lumen.

2. The device of claim 1, wherein the sealing assembly comprises an overflow port for exit of excess liquid and wherein the torque tube extends through the overflow port.

3. An aspirating catheter device having a liquid seal assembly that uses liquid as a sealing medium to prevent air or other fluids from contacting moveable catheter components in the area of a proximal end of a torque tube, the aspirating catheter device comprising:
   a housing providing at least one sealing site;
   a catheter having a proximal end terminating at a fixed joint within the housing at an aspiration site and a distal end terminating at an operating head and forming an aspiration lumen;
   a torque tube operably connected at a proximal end to a drive system for rotation and at a distal end to the working head, at least a portion of the torque tube being positioned in the housing;
   a stationary liner surrounding the torque tube and positioned within the catheter in a stationary relationship to the catheter, the liner extending from the at least one sealing site in the housing longitudinally less than the axial length of the torque tube and terminating distally at an intersect area located proximal to the distal end of the torque tube and within the aspiration lumen;
   a liquid flood space located between the liner and the torque tube; and
   an infusion port provided in the housing and supplying liquid to the liquid flood space; whereby liquid infused into the liquid flood space during operation of the aspirating catheter device forms a seal around the proximal end of the torque tube and exits the liquid flood space at the intersect area within the aspiration lumen.

4. The device of any one of claims 3 and 1, wherein the liquid flood space includes a clearance area between the liner and torque tube.

5. The device of any one of claims 3 and 1, wherein the torque tube is a coiled drive shaft and the liquid flood space includes gaps between the coils.

6. The device of any one of claims 3 and 1, wherein the torque tube includes a lumen for a guide wire and the liquid flood space includes the lumen.

7. The device of claims 3 and 1, further comprising a suction port for aspirating fluid from the aspiration lumen and wherein the pressure in the liquid flood space is lower than the pressure outside or proximal to the flood space during operation of the device.

8. The device of any one of claims 3 and 1, wherein proximal portions of the torque tube and liner are positioned in a hand held unit.

9. The device of any one of claims 3 and 1, wherein the inner diameter of the liner is from about 0.030 to about 0.040 inch.

10. The device of any one of claims 3 and 1, wherein the length of the liner is more than about 6 inches.

11. The device of any one of claims 3 and 1, wherein the liner comprises a thin, tough, flexible polymer-based tubing material.

12. The device of claim 11, wherein the liner comprises polyimide tubing and has a lubricious coating.

13. The device of any one of claims 3 and 1, wherein proximal portions of the torque tube and liner are positioned in the housing in a manner that permits free rotation and axial translation of the torque tube.

14. The device of any one of claims 3 and 1, wherein the length and diameter of the liner are selected to reduce the rate of flow in the proximal to distal direction in the liquid flood space and reduce the requirement for precise diametrical tolerances during operation of the device.

15. The device of any one of claims 3 and 1, wherein the working head is a cutting head.

* * * * *